United States Patent [19]

Steltenkamp

[11] Patent Number: 5,015,665
[45] Date of Patent: May 14, 1991

[54] N-ALKYL NEOTRIDECANAMIDE INSECT REPELLENT COMPOSITIONS

[75] Inventor: Robert J. Steltenkamp, Somerset, N.J.

[73] Assignee: Colgate-Palmolive Co., Piscataway, N.J.

[21] Appl. No.: 264,936

[22] Filed: Oct. 31, 1988

Related U.S. Application Data

[60] Division of Ser. No. 71,305, Jul. 16, 1987, Pat. No. 4,804,683, which is a continuation-in-part of Ser. No. 894,985, Aug. 8, 1986, abandoned.

[51] Int. Cl.$^5$ ............................................. A01N 37/18
[52] U.S. Cl. .................... 514/625; 514/629; 514/919
[58] Field of Search ...................... 514/625, 629, 919

[56] References Cited

U.S. PATENT DOCUMENTS

| | | | |
|---|---|---|---|
| 4,153,676 | 5/1979 | Rowstell et al. | 424/45 |
| 4,497,715 | 2/1985 | Bauman | 252/8.8 |
| 4,682,982 | 7/1987 | Steltenkamp et al. | 252/8.8 XR |

*Primary Examiner*—Leonard Schenkman
*Attorney, Agent, or Firm*—Bernard Lieberman; Murray M. Grill; Robert C. Sullivan

[57] ABSTRACT

N-lower alkyl neoalkanamides of 1 to 4 carbon atoms in the lower alkyl thereof, and of 12 to 14 carbon atoms in the neoalkanoyl group, e.g., N-methyl- and N-ethyl neotridecanamides, are new compounds which have insect repellent properties, being especially effective against cockroaches, e.g., the German and American cocoroaches. However, they are also useful as repellents for other insects, including mosquitoes, moths, flies, fleas, ants, and lice. Additionally, they may repel arachnids, such as spiders, ticks and mites. The new neoalkanamides may be synthesized easily, as by reacting a primary lower alkyl amine with a neoalkanoyl halide, e.g., by reacting methyl amino or ethyl amine with neotridecanoyl chloride. The most effective of the described amides for insect repellency, N-methyl neotridecanamide, is normally liquid and is sufficiently volatile to be detectable in air by insects. The neoalkanamides may be applied directly to surfaces to be treated or they may be incorporated in particulate or liquid compositions; in any such cases they are substantive to the surfaces to be made insect repellant; and they are of long lasting effects often repelling insects for two weeks after application. They are stable during normal uses, relatively low in manufacturing cost, of high substantivities to substrates, economical to use, unobjectionable, even pleasant in odor to humans, and safe to humans and animals, and to the environment.

13 Claims, 1 Drawing Sheet

FIG. 1

N-ALKYL NEOTRIDECANAMIDE INSECT REPELLENT COMPOSITIONS

This application is a division of my application Ser. No. 071,305, field July 16, 1987, which is now U.S. Pat. No. 4,804,683, which issued on Feb. 14, 1989, which was a continuation-in-part of my application Ser. No. 894,985, filed Aug. 8, 1986, now abandoned.

This application is a continuation-in-part of my application Ser. No. 894,985, filed Aug. 8, 1986.

This invention relates to N-alkyl neotridecanamides, which are novel chemical compounds that possess insect repelling properties. The mentioned neoalkanamides, especially N-methyl neotridecanamide, have been found to be effective in repelling insects, such as German cockroaches, when applied to surfaces of structures, items and materials to be protected against infestation by such insects. The present invention also relates to various compositions containing such N-alkyl neotridecanamides, which compositions are employed as means for depositing such active compounds onto surfaces to be made repellent to insects.

Most of the useful insect repellents reported in the literature are tertiary amides and of these the one heretofore regarded as the most effective all-purpose insect repellent is N,N-diethyl-m-toluamide, which is often referred to as "DEET". However the present neoalkanamides are also effective repellents, and N-methyl neotridecanamide, in particular, is superior to DEET in long lasting effectiveness. Additionally, such neoalkanamide is also effective to repel other insects, including the American cockroach. In view of the relatively small number of useful insect repellents known, efforts continue to be made to discover additional repellents which would be of greater repellent actions and of longer lasting effects. Desirably, such compounds also would be of improved physical characteristics, such as of more pleasant aroma, desirable volatility, non-staining character, liquid state (preferable), improved stability, greater substantivity to substrates, and longer lasting repellent effect.

In accordance with the present invention N-alkyl neoalkanamides that are intended for use as insect repellents have been discovered, in which the alkyl thereof is of 1 to 18, preferably 1 to 4 carbon atoms, more preferably 1 or 2 carbon atoms, and most preferably, methyl, and the neoalkanoyl moiety is of 12 to 14 carbon atoms, preferably 13. The most preferred of such compounds for employment as an insect repellent, especially effective against German and American cockroaches, is N-methyl neotridecanamide. Also within the invention are detergent compositions (both particulate and liquid), carpet and upholstery shampoos, human hair shampoos, hard surface cleaners, and soap and detergent bars comprising such N-alkyl neoalkanamide(s). Also useful are solutions and dispersions of the neoalkanamide(s) in liquid media or the neoalkanamides dispersed in a particulate or powdered carrier, which particulate or liquid products are suitable for application to a location from which insects are to be repelled. Also within the invention are processes for repelling insects by applications of insect repelling amounts of neoalkanamides of this invention to or near a surface, area, location or item from which such insects are to be repelled. In some situations the present repellents may be used in conjunction with insecticides, to repel the insects from one area and toward the location of the insecticide. Alternatively, they may be formulated with insecticides so that after the repellent effect is lost the treated area will still not be safe for insects.

Computer and manual searches of the prior art have not resulted in the finding of any reports of volatile primary or secondary amides that were recognized to be useful as insect repellents. Such searches indicated that the N-lower alkyl neoalkanamides of the present invention are novel and unobvious. The closest compounds to the N-lower alkyl neotridecanamides of this invention appear to be those described in U.S. Pat. No. 4,682,982, issued July 28, 1987, which relates to N-higher alkyl neoalkanamides, as antistatic agents, and U.S. patent application Ser. Nos. 894,983 (Steltenkamp and Eaton) filed Aug. 8, 1986, which relates to N-lower alkyl neoalkanamides as perfume components, and 894,985 (Steltenkamp) filed Aug. 8, 1986, which relates to lower alkyl neoalkanamides as insect repellents, but does not specifically claim the N-lower alkyl neotridecanamides, which have been found to be most effective for such purpose. Such applications are incorporated by reference.

The N-lower alkyl neoalkanamides of this invention can be considered to include those wherein the alkyl is of 1 to 18 carbon atoms, but preferably such alkyl will be of 1 to 4 carbon atoms, more preferably one or two carbon atoms (methyl) or ethyl), and most preferably such will be methyl. The neoalkanoyl moiety will be neotridecanoyl, which may be obtained from any suitable source, such as neotridecanoic acid. Such acid is obtainable from Exxon Chemical Americas, which identifies it as ECR-903. It is a mixture of neoacids of 12 to 14 carbon atoms, averaging about 13 carbon atoms, and will be referred to herein, for simplicity, as neotridecanoic acid. The corresponding alkyl neoalkanamides thereof, such as the methyl and ethyl neoalkanamides, may be made from such neoalkanoic acid by direct or indirect reaction with a suitable amine, such as methyl amine or ethyl amine. Usually the alkyl groups of the neotridecanamides are straight chain but they can also branch. Pure neoalkanamides of the types described may be made but often the commercial or technical grade acids, which may be used, and the amides made from them, will be mixtures.

The invented amides are of the formula wherein R, R' and R" are alkyl groups, the sum of the carbon atom contents of which is in the range of 10 to 12, and R'" is an alkyl, preferably a lower alkyl group, such as one of 1 to 4 carbon atoms. Further details with respect to R, R' and R" will be given later, in conjunction with a description of the neoalkanoic acid which may be employed as a starting material for the production of the present neoalkanamides.

An infrared absorption spectrum for the preferred N-methyl neotridecanamide of this invention is shown in the drawing, FIG. 1.

To make the neoalkanamides of this invention neotridecanoyl chloride reactant is slowly reacted with the appropriate primary amine, such as methyl amine, in ethyl ether, after which reaction the reaction mixture is washed with distilled water, dilute hydrochloric acid solution, dilute sodium hydroxide solution, and more distilled water, until it is neutral to pH paper. The ether is then removed by means of a steam bath, followed by employment of a vacuum evaporator. The reaction product obtained is light in color and is essentially pure. In an alternative method, the neotridecanoic acid may be reacted directly with the lower alkylamine.

As was previously mentioned, neotridecanoic acid is available from Exxon Chemical Americas, which synthesizes it by reacting a suitable branched alkene and carbon monoxide under high pressure at elevated temperature in the presence of aqueous acidic catalyst (Koch reaction). The general mechanism involved includes generation of carbonium ion, followed by complexation with carbon monoxide and the catalyst to form a "complex", which is subsequently hydrolyzed to generate free acid. The formula of the free acid is In neotridecanoic acid, for example, the total number of carbon atoms in R, R' and R'' is in the range of 10 to 12, averaging about 11. The acyl chloride starting material for the reaction to produce the invented N-lower alkyl neoalkanamide may be made from neotridecanoic acid and a suitable chlorinating agent, such as phosphorus trichloride or thionyl chloride, by known methods. Such compounds may be available from manufacturers other than Exxon Chemical Americas, such as Pennwalt, Inc., Lucidol Division, or White Chemical Corporation.

Although it is possible for the insect repellents of this invention to be incorporated in various materials when such materials are being manufactured, as by being mixed in with pulp for making paper, rubber and synthetic organic polymeric plastic batches, and chips for the manufacture of pressed boards, and while the invented insect repellents may also be injected or otherwise inserted into the bodies of items to be made insect repellent, usually the insect repellents will be applied to surfaces of areas, structures or items to be made insect repellent, either by direct application of the insect repelling N-alkyl neoalkanamide, in liquid solution or dispersion, or dispersed in a powdered carrier, or in a detergent composition, such as a laundry detergent, floor or wall cleaner, upholstery or rug shampoo, hair shampoo, liquid soap, bar soap, or in any other appropriate composition in which it may be usefully incorporated. Among such other appropriate compositions may be mentioned insecticidal and antibacterial washes or dips for humans, pets and farm animals, furniture polishes and finishes, floor waxes and finishes, ointments, salves and topical medicaments, insecticides, fungicides, bactericides, plant fertilizers, mulches and plant potting preparations, to name only a few. In some instances means will be provided for recharging such items and compositions with the active alkanamide component to renew their repellent effects. In the majority of instances the invented compositions will be applied directly or indirectly by external application to surfaces to be treated and afterward such application will be made on a continuing basis to maintain a satisfactory degree of insect repellency. Thus, the insect repellent N-alkyl neoalkanamide, such as N-methyl neotridecanamide, may be painted onto a surface to be treated or it may be applied to such a surface by washing it with a detergent composition containing the active insect repellent. The invented compounds are in liquid state or pasty condition at normal ambient temperatures and are water insoluble, so they tend to be satisfactorily substantive to surfaces from detergent compositions and from other preparations, even when such compositions are rinsed off, and normally, after either direct or indirect application to such surfaces, a sufficient amount of the alkanamide will remain to be effectively insect repelling. While different application rates of the different alkanamides of this invention are desirably used for effective repelling of different insects from different surfaces under different conditions, it is generally considered that insect repellent effects are obtainable at surface concentrations of the active ingredient in the range of 0.002 to 100 g./sq. m. For economic reasons and for effectiveness against more insects there will normally be applied from 0.01 to 5 g./sq. m., preferably 0.1 to 2 g./sq. m., e.g., 1 g./sq. m., as if roach repellency is desirable. Higher application rates, such as 10 to 100 g./sq. m., may be used against mosquitoes.

Because the present insect repellents are volatile their presence can be detected in the air near a surface to which they have been applied. Therefore, not only are the surfaces repellent to insects, which will avoid having their body parts contact such surfaces, but the vapors from the N-lower alkyl neoalkanamides will tend to repel insects from the surrounding space. Thus, the application of the volatile repellent to walls of a china closet can repel roaches from the closet interior, thereby preventing them from contacting, soiling and contaminating contained dishes, utensils and silverware. Similarly, coating of pantry surfaces, interior and/or exterior, with a furniture polish containing an invented volatile repellent, or use of shelf paper containing a repellent neoalkanamide can discourage roaches from entering the pantry and contaminating foods contained therein. Also, washing of clothing with detergent compositions containing the invented repellents may prevent insects from lighting on the clothing and its wearer, and from stinging or biting the wearer. Shampooing of a rug with a rug shampoo or carpet cleaner containing the invented repellent will discourage insects from entering the room and from nesting and laying their eggs in or under the rug. Washing of floors and walls with insect repellent detergent compositions formulated for such purpose will deposit thereon a substantive coating of the invented insect repellent and will discourage insects from contacting the floor and wall surfaces and from entering the treated rooms. It is an important feature of the invented insect repellents that although they are sufficiently volatile to be effective, their repellent properties are persistent, often lasting as long as three weeks or more (even longer if incorporated interiorly in a product) The invented repellents may be formulated with insecticides, such as by being sprayed onto the surfaces of insecticidal powders, e.g., boric acid powder, which is effective against roaches. By use of the neoalkanamide-boric acid composition immediate effectiveness in repelling the roaches is obtained and subsequently, after the repellent activity may have diminished, due to exhaustion by volatilization, any roaches that return to the area will be killed by the insecticide. It is recognized that a more normal practice is to incorporate an attractant with the insecticide but the repellent-insecticide composition also has utility.

It is apparent from the foregoing brief description that the invented insect repellents can be used in many compositions and can be applied in diverse ways. However, among the most useful products which can incorporate the invented neoalkanamides are detergent compositions, from which the neoalkanamides are surprisingly substantive to the surfaces of washed items. Such detergent compositions operate in several ways to counter insect contamination of the washed item. They remove any earlier contamination, remove stains and soils, on which the insects might feed, and which could attract them, and leave behind the insect repelling neoalkanamide.

The primary component of the present detergent compositions, other than the insect repelling neoalkanamide, is an organic detergent material. Such material may be one of the soaps, preferably a sodium and/or potassium higher ($C_{10-18}$) fatty acid soap, but is preferably a synthetic organic detergent, which may be of the anionic, nonionic, amphoteric, ampholytic, zwitterionic or cationic type, or may be a mixture of two or more detergents within one or more of such classifications. Preferably, the detergent will be a synthetic organic detergent of the anionic or nonionic type and often the anionic detergents will be most preferred. Descriptions of many such detergents are found in the text *Surface Active Agents and Detergents*, Vol. II, pages 25–138, by Schwartz, Perry and Berch, published in 1958 by Interscience Publishers, Inc. Such compounds are also described in a 1973 publication by John W. McCutcheon, entitled *Detergents and Emulsifiers*. Both such publications are hereby incorporated by reference.

The anionic detergents employed may be any such suitable detergents (or soaps), but normally will be salts of alkali metals, such as sodium or potassium or ammonium or lower alkanolammonium salts, e.g., triethanolamine salts. The anionic detergent may be a sulfate, sulfonate, phosphate or phosphonate or salt of other suitable acid but usually will be a sulfate or sulfonate, which may be designated as "sulf(on)ate". The anionic detergents will include a lipophilic group, which will normally have from 10 to 18 carbon atoms, preferably in linear higher alkyl arrangement, but other lipophilic groups may be present instead, preferably including 12 to 16 carbon atoms, such as branched chain alkyl benzene. In some cases the anionic detergents may include poly-lower alkoxy groups, as in ethoxylated higher fatty alcohol sulfates, e.g., triethoxylated lauryl alcohol sulfate. Normally the number of ethoxy groups in such detergents will be in the range of 1 to 30, preferably 1 to 10. As examples of suitable anionic detergents there may be mentioned: higher fatty alcohol sulfonates, such as sodium tridecyl sulfonate; sodium linear alkyl benzene sulfonates, e.g., sodium linear tridecylbenzene sulfonate; olefin sulfonates; and paraffin sulfonates. All of the anionic detergents will preferably be sodium salts for most of the particulate detergent compositions of this invention but potassium, ammonium and triethanolammonium salts may be more desirable for some liquid compositions Usually the detergent will preferably include a lipophilic alkyl moiety of 12 to 16 carbon atoms, often preferably of or averaging 12 to 13 carbon atoms The suitable nonionic detergents will normally be condensation products of lipophilic compounds or moieties and lower alkylene oxides or polyalkoxy moieties Highly preferable lipophiles are higher fatty alcohols of 10 to 18 carbon atoms but alkyl phenols, such as octyl and nonyl phenols, may also be used. The alkylene oxide of preference is ethylene oxide and normally from 3 to 30 moles of ethylene oxide will be present per mole of lipophile.

In the built detergent compositions, in which builders are employed to imprOve the detergency of the synthetic organic detergent (or soap), there will be present a building proportion of a suitable builder. Builders used may be inorganic or organic, water soluble or water insoluble. Among such classes of builders may be mentioned water soluble inorganic salts, including polyphosphates, e.g., sodium tripolyphosphate; carbonates, e.g., sodium carbonate; bicarbonates, e.g., sodium bicarbonate; borates, e.g., borax; and silicates, e.g., sodium silicate; water insoluble inorganic builders, including zeolites, e.g., hydrated Zeolite 4A; and water soluble organic builders, including citrates, gluconates, NTA, and polyacetal carboxylates. In some cases, as when mildness of the product to the human body or to delicate fabrics is important, alkaline builders and other "harsh" builders will be avoided, and in some cases no builders will be present at all.

Various adjuvants may be present in the detergent compositions of this invention to improve various characteristics of such products Thus, for example, bentonite may be employed as a fabric softener, perfumes and colorants may be added for their aesthetic effects, soil anti-redeposition agents may be employed, such as sodium carboxymethyl cellulose, and solvents or co-solvents may be present, as in liquid compositions. Among other adjuvants there may be mentioned fluorescent brighteners, antistatic agents, antibacterial agents, fungicides, foaming agents, anti-foams, flow promoters, suspending agents, antioxidants, anti-gelling agents, soil release promoting agents, and enzymes.

The detergent compositions of this invention may be in particulate, powder, tablet, bar, liquid, paste, gel, capsule, leaf, foam or "aerosol" or other suitable form, as may be best suited for the purpose intended Methods for manufacturing products in such forms are well known in the art of processing soaps and detergents, and need not be further mentioned here.

While it is possible to apply the present insect repelling N-lower alkyl neoalkanamides directly to surfaces and items to be made insect repellent, in particulate form, on or mixed with particulate carrier, it is often more convenient and also more efficacious to utilize the repellent neoalkanamide as a liquid solution or emulsion. To make such solutions the neoalkanamide may be dissolved in any suitable solvent, such as a lower alcohol, e.g., ethanol, or an aqueous alcoholic medium. Of course, other solvents may also be employed, such as hydrocarbons, esters, ketones, aldehydes and halogenated hydrocarbons. Among the hydrocarbons and halogenated hydrocarbons there may be mentioned isobutane and the chlorofluorinated lower hydrocarbons, such as dichlorodifluoromethane, monofluorotrichloromethane and other chlorofluoromethanes, -ethanes and -propanes. Such compounds include the liquefiable gases, which can be maintained in liquid state in pressurized dispensing containers, for ready application as sprays or in other suitable forms to locations which are to be made insect repellent. The neoalkanamides may also be in aqueous or other emulsion form, when a suitable emulsifier, hydrotrope or surface active agent is utilized, too. The invented neoalkanamides may also be dispersed in particulate or powdered inert or active materials. Among such insert materials may be mentioned silica, calcium carbonate, clay, expanded polystyrene, wood chips and sawdust. Also, the neoalkanamides may be dispersed in active materials, such as detergent composition beads, bentonite (a fabric softener) and boric acid (a roach poison).

Other modes of use of the invented insect repellents, some of which have already been mentioned, include incorporation in materials which are intended for use at or near sites from which the insects are to be excluded. Thus, the repellents may be incorporated in shelf papers, wallpapers, wallpaper glues, rugs and carpeting, and carpet padding. They may be formulated in floor waxes, furniture polishes and other preparations that are intended for applications to surfaces in the areas to be treated They may be automatically dispensed in certain areas, such as storerooms and warehouses, by timer-operated sprayers or other dispensers, and they may be renewably charged to containers, from which they may be vaporized, such as absorbers and other holders, as in the under sides of garbage can covers.

The detergent compositions of this invention, including those that are useful for washing hard surfaces, such as floors, and also soft surfaces, such as those of carpets, laundry, and human hair, will include an insect repelling proportion of N-alkyl neoalkanamide or a mixture of such neoalkanamides, which proportion is sufficient so that enough of the neoalkanamide is retained on the washed surface, after washing of it with the detergent composition, to repel insects from such surface, and will also include a detersive proportion of soap or synthetic organic detergent (or any suitable mixture thereof). The neoalkanamide is preferably one wherein the lower alkyl is of 1 to 4 carbon atoms (and that designation includes mixed lower alkyls, too, averaging such numbers of carbon atoms), more preferably being methyl or ethyl, and usually and preferably being methyl. The neoalkanoyl moiety of the neoalkanamide is of 12 to 14 carbon atoms, preferably of 13 carbon atoms.

In particulate built laundry detergent compositions of the invention the active detergent component will usually be synthetic organic detergent selected from the group consisting of anionic, nonionic, amphoteric, ampholytic, and zwitterionic detergents and mixtures thereof, and the builder will be water soluble inorganic or organic builder or water insoluble inorganic builder. The proportions of synthetic organic detergent(s), builder(s), and neoalkanamide(s) to make an effective insect repellent particulate synthetic organic detergent composition will be 1 or 5 to 35%, 10 to 90%, and 0.2 to 10%, respectively. In concentrates, intended for dilution (usually with water) before use, the N-methyl neotridecanamide or N-lower alkyl neotridecanamide component content may be as high as 25%, e.g., 10 to 25%, so such content may be from 0.2 to 25% in the described laundry detergent compositions (regular and concentrated). Preferred detergent compositions of such type will have the synthetic organic detergent selected from the group consisting of anionic and nonionic detergents, and mixtures thereof, may contain water soluble filler salt(s), such as sodium sulfate, and will contain a methyl- or ethyl neotridecanamide, or a mixture thereof. The proportions of such components for best effects in such unconcentrated detergent compositions will often be 7 to 30% of the synthetic organic detergent(s), 20 to 75% of the builder salt(s), 0 to 50% of the filler salt(s), and 0.5 to 5% of the neoalkanamide(s).

When liquid detergents containing the invented insect repellent neoalkanamide(s) are made, the same components may be used, plus a liquid medium, but the detergent will preferably be non-soap. Sometimes a conventional emulsifying agent, such as an Emcol®, sold by Witco Chemical Co., Inc., will be employed, in emulsifying proportion. Also, hydrotropes, such as sodium toluene sulfate, and other functional and aesthetic adjuvants, such as have been employed in liquid detergent compositions, and/or fillers, may be included, or not. In the built liquid detergents the synthetic organic detergent content will be in the range of 2 to 25%, the builder content will be 5 to 40%, the neoalkanamide content will be 0.2 to 10%, and the liquid medium content, preferably aqueous, will be 40 to 90%. More preferably, the built liquid detergent compositions of the invention will comprise 3 to 20% of a synthetic organic detergent which is anionic and/or nonionic, 10 to 30% of builder salt(s) for such detergent(s), which may be water soluble, such as potassium pyrophosphate, sodium carbonate, or sodium polyacetal carboxylate, and/or water insoluble, such as sodium zeolite, 0 to 20% of water soluble filler salt, such as sodium sulfate, 0.5 to 5% of N-methyl neotridecanamide and/or N-ethyl neotridecanamide, and 50 to 90% of water, preferably deionized water. For concentrated products the N-lower alkyl neotridecanamide content may be as high as 25%, so the range of contents of such alkanamide may be 0.2 to 25%, and 0.5 to 25%.

When an insect repelling shampoo for use on upholstery, rugs and carpets is to be made, it may comprise 1 to 35%, preferably 5 to 20%, of a detergent selected from the group consisting of water soluble soap(s) and synthetic organic detergents, 0 to 40% of builder(s) for the soap and/or detergent, often preferably 0%, and 0.2 to 10% of N-lower alkyl neoalkanamide (up to 25% for shampoo concentrates), preferably 0.5 to 5%, in a liquid medium, preferably aqueous, the percentage of which may be in the range of 40 to 90%, preferably 70 to 90%, with water being 50 to 90% of the composition, preferably 70 to 90%. Alternatively, the shampoo may be in gel, paste or powder form.

When the present insect repellents are used in shampoos intended for washing human hair on the head and for making the hair repellent of insects, the shampoos will preferably comprise 2 to 25% of soap and/or the previously described synthetic organic detergent(s), and 0.2 to 10% (up to 25% for concentrates) of N-lower alkyl neoalkanamide, in an aqueous medium such as 40 to 90% of water, preferably deionized water. The aqueous medium may include up to half thereof of a cosolvent, such as a lower alkanol, e.g., ethanol, or a glycol, but normally the percentage of such co-solvent will be limited to 5 to 20% of the final product. In more preferred embodiments of the shampoos for human hair, there will be present 5 to 22% of synthetic organic detergent, 0 to 20% of water soluble filler salt, 0.5 to 5% of N-lower alkyl neodecanamide or mixture thereof, and 50 to 90% of water, preferably deionized.

Solid or bar or cake insect repellent detergent products can also be made, which may be used for washing persons, animals, laundry, rugs, and/or hard surfaces, such as walls and floors, to make them insect repellent. Such products can comprise neoalkanamide repellent with soap and/or synthetic organic detergent, or may also include builders, fillers and other adjuvants, previously referred to herein The proportion of N-alkyl neoalkanamide in such products will normally be from 0.2 to 10%, and that of the detersive material will be from 15 to 95%. Such bars will normally be of a moisture content in the range of 2 to 20% and the balance will be of builder(s) and/or filler(s) and/or adjuvant(s), when such are present. Normally, the adjuvant(s) content of the various detergent products will be in the range of 0.5 to 20%, total, with individual adjuvants being 0.1 to 5% for the most part.

The various detergent compositions described above may be prepared by processes that are well known in the art and need not be described at length herein. Such processes include spray drying, dry mixing, spray applying and/or coating, sequential dissolving and/or dispersing and/or emulsifying, milling, plodding and pressing.

When the insect repellent is to be sprayed or applied in a carrier, such as a liquid or particulate material or medium, the concentration of it therein will be an insect repellent proportion, so that when applied onto a surface of a material to be treated (or into the interior or other portion thereof), by spraying, dusting, rubbing, wiping, pouring, depositing, or other mechanism, the repellent applied will be in such quantity and/or concentration that it will be effective in repelling insects or a particular type of insect, so that such insect(s) will stay away from the treated location. Such repelling is due to the insect being reluctant to contact the repellent and also in some measure is due to the repellent effect of the vapor from the repellent, which is at least partially volatile, although it may last for as long as two weeks or more, as normally applied, using the application concentrations that were previously given. Also, the repellent lasting power is increased when it is incorporated in the body of an article, such as in a mattress or absorbent sponge, rather than only on a surface that is exposed to the air.

The concentration of the repellent chemical(s) in a liquid medium, such as an aqueous medium, in which a dispersing agent or emulsifier may be employed, too, will usually be in the range of 0.2 to 10, 25 or 50%, but is often preferably in the range of 0.5 to 10%, e.g., about 1% or 5%, for roach repellency. The liquid medium may be water, lower alkanol, such as ethanol, lower ketone, such as acetone, lower hydrocarbon, such as isobutane, cyclopropane or mixture thereof, or halogenated lower hydrocarbon, such as chlorofluorinated, fluorinated or chlorinated lower hydrocarbons, e.g., Propellants 11 and 12. The various "lower" compounds are of 1 to 4 carbon atoms per molecule, preferably 1 or 2 carbon atoms, and in the case of those that are normally in the gaseous state, they are under sufficient pressure to maintain them in liquid state.

Similar concentrations of the invented repellents may be employed in powdered or particulate carriers. Thus, the invented neoalkanamides may be applied as by spraying of liquid droplets onto powdered calcium carbonate, silica, clay or boric acid, onto grains of such materials, or onto detergent composition particles or synthetic organic polymer beads (preferably of particle sizes between 125 microns and 2.4 mm. in diameters), in concentrations in the range of 0.2 to 10 or 25%, preferably 0.5 to 5 or 10% for roach repellents.

In insect repelling processes or treatments in which the invented repellents are employed they will normally be applied to surfaces to be treated at concentrations such that 0.002 to 100 g./sq. m. initially remain on such surfaces after treatment, with such application rate preferably being 0.01 to 5 or 10 g./sq. m. and more preferably 0.1 to 2 g./sq. m., e.g., 1 g./sq. m. for action against roaches. Concentrations outside surcharges may sometimes also be of at least partial effectiveness When the repellent is in a detergent composition which is employed in an aqueous washing medium, such as water, the wash water will usually contain from 0.05 to 5% of the detergent composition but in some applications, such as shampooing of human hair or of carpets or rugs with foam preparations, the concentration may be greater, sometimes being as high as 25%.

When the repellents are incorporated in and applied to surfaces in other media or preparations, such as waxes or furniture polishes, the concentrations thereof will usually be in the same ranges as for detergent compositions, but may be increased, if desired, in some such instances to as high as 25%.

The invented repellents possess various significant advantages over various other repellent materials available. They are essentially non-toxic and therefore are not hazardous to children or pets that might come into contact with them, after application. They are pleasantly aromatic, with N-methyl neotridecanamide, for example, having a mild tobacco-like odor, and therefore do not usually adversely affect the aromas of preparations into which they are formulated. In fact, they may be useful in giving such preparations acceptable aromas, and thereby permit the omissions of expensive perfumes from such products. They are substantially colorless and therefore can be employed in detergents, shampoos, polishes, sprays, and various compositions and preparations wherein the imparting of color would not be acceptable. N-methyl neotridecanamide is effective both as a contact and a vapor repellent and is superior in repelling action to various commercial insect repellents, especially against German cockroaches, which are considered to be the most difficult household insect pest to control. They are also effective against American and Oriental cockroaches, and other insects. The present repellents are long lasting, with tests having shown N-methyl neotridecanamide to be effective to repel roaches for two weeks and more after topical application. It is expected that controlled tests will confirm that they are also effective against mosquitoes, moths (including larvae), flies and other insect pests, and compare well in repellency to a "standard" repellent, N,N-diethyl-m-toluamide (DEET). The N-lower alkyl neotridicanamides are sufficiently stable to be able to maintain their insect repelling properties despite being incorporated in various soap, detergent, polish, wax, insecticide, cosmetic, and coating preparations, in liquid, paste, gel, foam, powder, particulate or solid bar form, or in aqueous or other solvent solutions, emulsions or dispersions, and they are highly substantive from such media.

The following examples illustrate but do not limit the invention. Unless otherwise stated, all parts are by weight and all temperatures are in °C. in the examples, elsewhere in this specification, and in the appended claims.

EXAMPLE 1

Approximately stoichiometric proportions of Exxon Chemical Americas neo-tridecanoic acid (ECR-903), prime grade) and thionyl chloride (1% excess) are reacted in the presence of dimethyl formamide, employing 500 grams of the neotridecanoic acid and 291.5 grams of thionyl chloride, at 25° C., in a one liter, three-necked flask equipped with top stirrer and a condenser with an outlet dipping into an aqueous sodium hydroxide solution. As the thionyl chloride was added over a period of ten minutes there was no temperature increase and during the addition of the dimethyl formamide (9.4 grams), which was added over a period of ½ hour, the temperature dropped to 15° C. Subsequently the temperature was increased to 65° C. and was kept at that temperature for five hours. The product was distilled into three fractions, with the fraction distilled at temperatures in the range of 115° to 121° C., at 9.5 mm. of mercury, amounting to 402 grams and being colorless and water white. Such product, obtained in 74% yield, was confirmed by infrared analysis to be neotridecanoyl chloride, containing no appreciable proportion of neotridecanoic acid.

Figure 1:
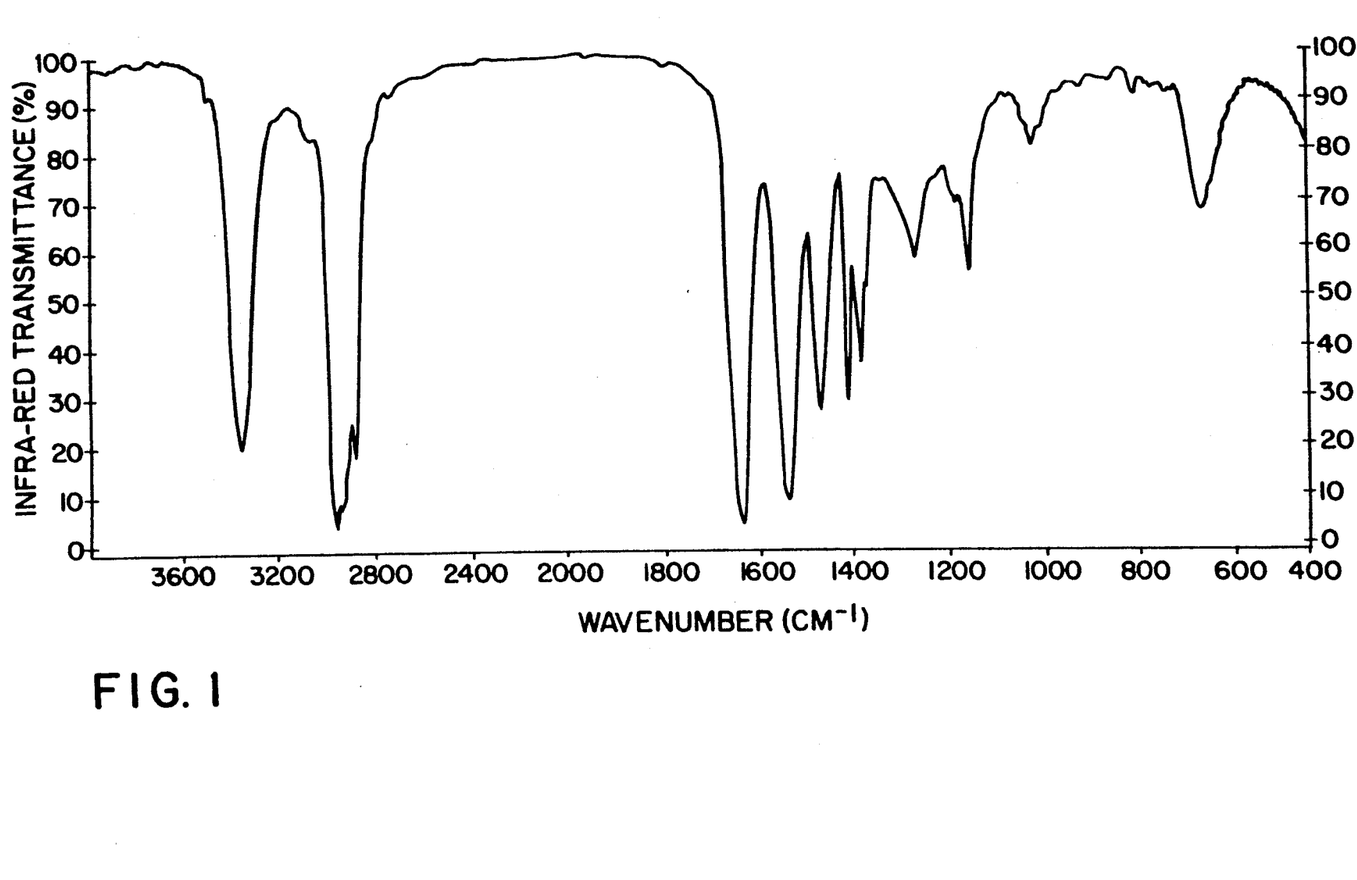

The neotridecanoyl chloride made was subsequently reacted with methyl amine in a three-necked, glass, one-liter flask equipped with a Chesapeake stirrer, a thermometer, an addition funnel and a condenser equipped with a desiccant tube. The flask was placed in a ice bath and was charged with 350 grams of neotridecanoyl chloride (the manufacture of which is described above), 68.4 grams of a 40% aqueous solution of methyl amine and 161.9 grams of triethyl amine, which serves to remove any hydrochloric acid produced during the reaction. The neotridecanoyl chloride was added dropwise to the flask containing the amines over a period of about an hour and after completion of such addition the reaction mixture was allowed to reach room temperature, after which the reaction mixture was separated into two layers at 40° C., the top layer was water washed, the colorless emulsion resulting Was stripped at 80°-90° C. for one hour, employing a rotary evaporator at 1.5 mm. of mercury, the product was acid washed and alkali washed, and subsequently was washed twice with distilled water. The product resulting was pure and water white N-methyl neotridecanamide. An infrared spectrograph of the product is shown in FIG. 1. The name given describes the N-methyl amide of neotridecanoic acid, which acid is a neoalkanoic acid of 12 to 14 carbon atoms, averaging about 13 carbon atoms per molecule.

In similar manners there may be made N-ethyl neotridecanamide, N-isopropyl neotridecanamide, N-n-propyl neotridecanamide, N-t-butyl neotridecanamide, N-n-butyl neotridecanamide and N-isobutyl neotridecanamide, using essentially stoichiometric proportions of appropriate alkyl amines and neotridecanoyl chloride. Diethyl ether may be employed as a solvent in the these reactions, when appropriate.

EXAMPLE 2

N-methyl neotridecanamide and N-ethyl neotridecanamide are made by the direct reaction of neotridecanoic acid and methyl or ethyl amine, with diethyl ether as a reaction solvent and without employing triethyl amine as a scavenger for acid. In such reaction a one-liter, three-necked flask is employed but the system is closed and the flask is equipped with a heating mantle, a magnetic stirrer, a source of nitrogen gas, with means for conveying it to below the surface of the reaction mixture, a thermometer and a thermostatic control, which holds the temperature of the reaction mixture at 240° C. or other suitable elevated temperature for five hours or optimum reaction time. Reaction products are separated, washed and have solvent removed from them in manners like that described in Example 1. The products resulting are N-methyl neotridecanamide, with a spectrograph like that of FIG. 1, and the corresponding N-ethyl neotridecanamide.

EXAMPLE 3

The N-methyl neotridecanamide made by the process of Example 1 was tested for cockroach repellency by dissolving one gram of it in 10 ml. of acetone and then swabbing the inside of a Dixie ® cup, having an internal surface area of 188.5 sq. cm., with the solution so that upon evaporation of the acetone there is left behind 0.0189 g. of the N-methyl neotridecanamide, evenly coating the cup interior at a concentration of 1.0 g./m². Four equidistant openings, are cut in the drinking end edges of the cup so that when the cup is inverted and placed on a flat surface, it will be possible for test insects (roaches) to crawl through them and under it. An identical control cup is prepared, with the sole difference being that the same proportion of acetone is applied to the cup and floor surface but no N-methyl neotridecanamide is present with it. Each cup is placed in the middle of a half of a medially dividable rectangular area in a box, to which box there are next added 100 cockroaches. The box top is transparent and the roaches cannot escape from the box. Initially the box is in the dark but to test the effectiveness of the repellent applied to the cup interior the box is illuminated with a 100 watt incandescent bulb positioned about 50 cm. above it. Each of the roaches, seeking to hide from the light, crawls under one of the inverted cups. It is considered that any significant difference in the number of roaches under the experimental and control cups indicates repellency or attraction effected by the experimental (because the control is essentially neutral, having nothing remaining on its surfaces). After waiting one minute after illumination, a divider is slid across the box separating the experimental and control areas, the cups are removed or knocked over, and the roaches in each section are counted. The number in the control area is the percentage effectiveness of the repellent. By this test, after an average of 14 days, N-methyl neotridecanamide is still 100% effective against the control and after 24 days it is still at least 60% effective. It is significantly more effective than DEET or another accepted cockroach repellent, MGK-874, and it is more effective than N-methyl neodecanamide, by this test, and in "head to head" comparisons in which the NMNDA, DEET or MGK-874 is applied to the "control" cup.

In the described tests results are the same whether the repellents are made by the direct condensation method, from neotridecanoic acid, or from the neotridecanoyl chloride. When other neoalkanamides of the invented types are employed, such as N-ethyl neotridecanamide insect repellency is also obtained but with respect to cockroach repellency it is less.

Instead of applying the repellents to the test surfaces in acetone solution they may be sprayed onto such surfaces by means of "aerosol" or pressurized sprays in 50:50 mixtures of isobutane and cyclobutane, or 60:40 solutions of Freon 12 and Freon 11 (dichloridifluoromethane and trichloromonofluoromethane, respectively, or in other pressurized solvents. Instead of applying the solutions as 11.2% solutions, by weight, as in the tests reported earlier in this example, concentrations in the range of 2% to 30% may often be used, depending to some extent on the solubility of the repellents in the solvent system employed, for example 15% in the Freon system, 20% in the hydrocarbon system, 5% in ethanol, and 25% in methyl ethyl ketone. Aqueous systems may also be used, preferably with emulsifiers or suitable surface active agents being present to hold the repellent in homogeneous suspension as colloidal droplets, with its concentration usually being somewhat lower than for the organic solvent solutions, e.g., 3%, 5% and 7%. All such liquid systems may be applied with the aid of cloths, pads, spray cans and nozzles, or gels or pastes can also be used.

In practical tests, on actual kitchen floors, counters, drainboards and walls, and in kitchen cabinets and dishwashers, and under refrigerators, in roach-infested apartments, significantly fewer roaches will be observed on surfaces to which or near which the invented repellents are applied than on control surfaces, and fewer roaches are found on the bottoms and shelves of cabinets and pantries when walls thereof are treated with the invented repellents, especially when the repellent is N-methyl neotridecanamide, indicating that the repellents are vapor-effective too, as well as contact-effective. When floors, walls, counters, sinks, cabinets, appliances, windows, doors, rugs and carpets in a house or apartment are treated with the invented repellents, e.g., N-methyl neotridecanamide or N-ethyl neotridecanamide, the incidence of cockroach infestation is reduced, compared to control apartments where no repellent is applied. However, because of the initial presence of the pests in the premises, control of them may take as long as a week or two, and sometimes can require several applications of the repellent. In some instances the application rates are desirably increased to as high as 10 g./sq. m. but in other instances such rates may be dropped to 0.01 g./sq. m. or lower. Of course, results are usually better with higher application rates.

EXAMPLE 4

(Built Particulate Detergent)

| Component | Percent |
| --- | --- |
| Sodium linear tridecyl benzene sulfonate | 20.0 |
| Sodium tripolyphosphate | 40.0 |
| Sodium carbonate | 10.0 |
| Sodium bicarbonate | 10.0 |
| Borax | 5.0 |
| Enzyme blend (proteolytic + amylolytic in powdered carrier) | 1.0 |
| Sodium carboxymethylcellulose | 0.5 |
| Fluorescent brightener | 1.0 |
| N-methyl neotridecanamide | 2.0 |
| Water | 10.5 |
|  | 100.0 |

All of the components of the detergent composition except the enzyme powder and repellent are mixed together in a crutcher slurry, which is spray dried to hollow globular bead form, of particle sizes in the range of No's. 10 to 100, U.S. Sieve Series. Subsequently, the enzyme powder is blended with the spray dried beads and the insect repellent, in liquid state, is sprayed onto the mixture, while it is being tumbled, to form a uniform composition.

EXAMPLE 5

(Scouring Cleanser)

| Component | Percent |
| --- | --- |
| Silex (finely divided silica powder) | 97.5 |
| Sodium linear dodecyl benzene sulfonate | 2.0 |
| N-methyl neotridecanamide | 0.5 |

-continued

| Component | Percent |
| --- | --- |
|  | 100.0 |

EXAMPLE 6

(Built Liquid All-Purpose Detergent)

| Component | Percent |
| --- | --- |
| *Nonionic detergent | 1.0 |
| Sodium linear dodecyl benzene sulfonate | 2.0 |
| Sodium cumene sulfonate | 5.0 |
| Sodium carbonate | 5.0 |
| Sodium bicarbonate | 1.0 |
| Fluorescent brightener | 0.02 |
| Dye | 0.01 |
| N-methyl neotridecanamide | 1.0 |
| Water (deionized) | 84.97 |
|  | 100.0 |

*Condensation product of 1 mole of higher fatty alcohol mixture averaging 10 carbon atoms, with 5 moles of ethylene oxide.

EXAMPLE 7

(Built Liquid All-Purpose Cleanser)

| Component | Percent |
| --- | --- |
| Sodium linear dodecylbenzene sulfonate | 3.7 |
| Sodium sulfate | 3.3 |
| Natural soda ash | 4.0 |
| Sodium bicarbonate | 2.0 |
| *Nonionic detergent | 2.0 |
| Isopropyl alcohol | 1.8 |
| Distilled coconut oil fatty acids | 0.5 |
| Dyes (as 0.1% aqueous solutions) | 0.6 |
| Perfume | 0.8 |
| Softened water | 80.3 |
| N-methyl neotridecanamide | 1.0 |
|  | 100.0 |

*Condensation product of one mole of a mixture of higher fatty alcohols of 9-11 carbon atoms, with 6 moles of ethylene oxide The pH of the insect repellent liquid all-purpose cleaner is adjusted with either sulfuric acid or caustic soda to be 10.5±0.2.

The product made is an effective insect repellent cleaner, and surfaces and articles washed with it or to which it is applied, as a concentrated or diluted product, are left with a minor proportion of N-methyl neotridecanamide insect repellent thereon, so such surfaces and articles become insect repellent.

EXAMPLE 8

(Liquid Pine Oil Cleaner)

| Component | Percent |
| --- | --- |
| Sodium paraffin sulfonate | 6.8 |
| Isopropanol | 7.0 |
| *Neodol ® 23-6.5 (Shell Chemical Corporation) | 4.0 |
| Pine oil | 10.0 |
| N-methyl neotridecanamide | 10.0 |
| Sodium sulfate | 3.8 |
| Deionized water | 58.4 |
|  | 100.0 |

*Condensation product of one mole of higher fatty alcohol mixture averaging 12 or 13 carbon atoms, with 6.5 moles of ethylene oxide When the above composition is used as a cleaner it leaves surfaces to which it has been applied, in concentrated or diluted form, insect repellent for periods up to three weeks.

EXAMPLE 9

(Carpet Cleaner)

| Component | Percent |
|---|---|
| Sodium salt of lauric monoethanolamide sulfosuccinate | 30.0 |
| Mixed lipolytic, proteolytic and amylolytic enzymes | 2.0 |
| Sodium tripolyphosphate | 20.0 |
| Sodium hexametaphosphate | 5.0 |
| Sodium monophosphate | 3.5 |
| Sodium bicarbonate | 20.0 |
| Urea | 8.0 |
| *Micro-Cel ® | 10.0 |
| N-methyl neotridecanamide | 1.5 |
| | 100.0 |

*Finely divided hydrated synthetic calcium silicate (Johns-Manville Products Corp.)

This product should be diluted 1:30 with water before use. One hundred grams will suffice to clean about ten square meters of soiled carpeting.

EXAMPLE 10

(Upholstery Cleaner)

| Component | Percent |
|---|---|
| *Sulframin OBS | 10.0 |
| Aqueous ammonia (28%) | 30.0 |
| Water | 58.5 |
| N-methyl neotridecanamide | 1.5 |
| | 100.0 |

*Linear alkylaryl sulfonic acid (Witco Chemical Corp.)

Before use this upholstery cleaner is mixed 1:3 by volume with Stoddard solvent.

EXAMPLE 11

(Hair Shampoo)

| Component | Percent |
|---|---|
| Ammonium monoglyceride sulfate | 22.0 |
| Hydroxypropyl methyl cellulose | 1.0 |
| Polyacrylamide | 1.0 |
| N-methyl neotridecanamide | 1.0 |
| Deionized water | 75.0 |
| | 100.0 |

EXAMPLE 12

(Skin Cream)

| Component | Amount (as indicated) |
|---|---|
| Yellow ceresin wax | 2.0 ounces |
| Yellow beeswax | 2.0 ounces |
| Stearic acid | 2.0 ounces |
| White petrolatum | 4.0 ounces |
| White mineral oil | 8.0 fluid ounces |
| Water | 6.0 fluid ounces |
| Borax | 0.3 ounce |
| Triethanolamine | 0.5 fluid ounce |

The ceresin, beeswax, petrolatum, stearic acid and white mineral oil are melted together by heating to 71° C. The borax is dissolved in hot water and the triethanolamine is added to the solution, with the temperature being raised to 71° C. The aqueous solution is poured into the melted wax mixture with stirring and stirring is continued as the mixture is removed from the heat. When it begins to thicken there are added to it 10 grams of N-methyl neotridecanamide.

EXAMPLE 13

(Body Lotion)

| Component | Parts |
|---|---|
| Glyceryl monostearate | 50.0 |
| Oleic acid | 30.0 |
| Mineral oil | 15.0 |
| Lanolin | 10.0 |
| Triethanolamine | 12.0 |
| Sodium lauryl sulfate | 10.0 |
| preservative | 10.0 |
| Water (deionized) | 980.0 |
| N-ethyl neotridecanamide | 12.0 |

EXAMPLE 14

(Bar Soap)

| Component | Percent |
|---|---|
| *Higher fatty acid soap | 88.0 |
| N-methyl neotridecanamide | 1.0 |
| Titanium dioxide | 1.0 |
| Preservative (stannic chloride) | 0.2 |
| Water | 9.8 |
| | 100.0 |

*80:20 tallow:coco sodium soap

Instead of soap bars and cakes, soap-synthetic bars can be made by substituting sodium coco-monoglyceride sulfate for up to 25% of the soap content of the formula. Similarly, by employing a suitable plasticizer all-synthetic detergent bars can be made.

Preservative, titanium dioxide, repellent and some water are milled with the dried soap chips (which contain about 8% water) and are plodded to bar form, after which the bars are cut to lengths and pressed to cake shape. Laundry bars can be made by adding 20 to 40% of builder salt, such as sodium tripolyphosphate and/or sodium carbonate to the formula, usually with an increase in the moisture content to improve plasticity during processing. Framed laundry bars and synthetic laundry bars can also be made and the content of the insect repellent will sometimes be increased in such bars, up to about 5%.

EXAMPLE 15

(Repellent Spray)

| Component | Percent |
|---|---|
| *Propellant 12 | 45.5 |
| **Propellant 11 | 45.5 |
| Mineral oil | 4.0 |
| N-methyl neotridecanamide | 5.0 |
| | 100.0 |

*dichlorodifluoromethane
**trichloromonofluoromethane

The mineral oil and insect repellent are dissolved in the pressurized propellant mixture and such mixture is pressure filled into a dispensing container equipped with a spray nozzle designed for optimum spraying of the repellent solution.

EXAMPLE 16

(Powdered Repellent)

| Component | Percent |
| --- | --- |
| Clay, powdered | 99.0 |
| N-methyl neotridecanamide | 1.0 |
| | 100.0 |

EXAMPLE 17

(Floor Wax)

| Component | Parts |
| --- | --- |
| Montan based ester wax | 6.0 |
| Polyethylene wax | 4.0 |
| Non-oxidized microcrystalline wax | 5.0 |
| Tall oil fatty acids | 0.2 |
| Aqueous potassium hydroxide solution (43%) | 0.5 |
| N,N-diethylaminoethanol | 1.0 |
| Methyl carbitol | 1.0 |
| N-propyl neotridecanamide | 2.0 |
| Water | 80.3 |
| | 100.0 |

EXAMPLE 18

(Aerosol Furniture Polish)

| Component | Parts |
| --- | --- |
| Carnauba wax | 5.0 |
| Beeswax | 5.0 |
| Ceresin wax | 5.0 |
| Silicone oil (DC 200) | 5.0 |
| Stoddard solvent | 40.0 |
| Sodium soap (75:25 tallow:coco) | 2.0 |
| Water | 130.0 |

A wax-silicone concentrate is made by heating the Stoddard solvent to a temperature of about 52° C. and gradually adding to it the pre-melted waxes and silicone oil with agitation. Concurrently, the soap is dissolved in the water at a temperature of about 90° C., after which the hot soap solution is admixed with the wax dispersion, under vigorous agitation. The mixture is then cooled rapidly to room temperature and 385 parts of water, 71 parts of naphtha and 15 parts of N-methyl neodecanamide are slowly added to it. 71 Parts of Propellant 12 are pressure loaded into dispensing containers after pre-loadings of the balance of the composition.

EXAMPLE 19

(Shelf Paper)

Rolls of shelf paper are sprayed on both sides thereof with liquid N-methyl neotridecanamide in volatile solvent, such as acetone, and are re-rolled after volatilization off of the solvent. The proportion of repellent is regulated to be 2%, although in some instances as little as 0.1% may be employed. The shelf paper has a long "shelf life" prior to use because loss of the repellent by volatilization is inhibited by the rolling of the paper. In a modification of this example the neoalkanamide repellent is added to the paper pulp during the manufacturing process but care must be taken not to drive off the repellent during and drying operations.

EXAMPLE 20

(Garbage Can Insect Repellent)

A 2% of N-methyl neotridecanamide in a sponge is made by injecting the N-methyl neotridecanamide into the interior of an open celled polyurethane foam, of flat cylindrical shape, which is inserted in an open holder affixed to the interior of the lid of a "step-on" kitchen waste container.

EXAMPLE 21

(Repellent-Insecticide)

| Component | Percent |
| --- | --- |
| Boric acid | 98.0 |
| N-methyl neotridecanamide | 2.0 |
| | 100.0 |

The various products of Examples 4–21 are all effective in repelling insects, especially German and American cockroaches. However, they represent only a few of the many compositions and articles of manufacture within the present invention.

The invention has been described with respect to various illustrations and embodiments thereof but is not to be limited to them because it is evident that one of skill in the art will be able to utilize substitutes and equivalents without departing from the invention.

What is claimed is:

1. An insect repelling composition, useful for repelling insects from an area, location or item, which comprises an insect repellent proportion of a compound of the formula wherein R''' is methyl and is neotridecanoyl, wherein the sum of the carbon atoms in R, R' and R'', all of which are alkyl groups, is eleven.

2. An insect repellent composition according to claim 1 wherein the insect repelling compound is dispersed in an aqueous medium a concentration in the range of 0.2 to 25%.

3. An insect repellent composition according to claim 1 wherein the insect repelling compound is dissolved in a liquid solvent medium at a concentration in the range of 0.2 to 25%.

4. An insect repellent composition according to claim 3 wherein the concentration of the insect repelling compound in the liquid solvent medium is in the range of 0.5 to 10% and the liquid solvent medium is a normally gaseous hydrocarbon or halogenated hydrocarbon under sufficient pressure to be in liquid state at room temperature.

5. An insect repellent composition according to claim 1 which is effective to repel insects from sites to which it is applied, at the rate of 0.1 to 10 grams per square meter, which comprises 0.2 to 50% of the insect repelling compound in a liquid aqueous or solvent medium.

6. An insect repellent composition according to claim 5 wherein the liquid medium is a $C_{1-4}$ chlorofluorocarbon or chlorofluorohydrocarbon and the concentration of the insect repelling compound in such liquid medium is in the range of 0.5 to 10%.

7. An insect repellent composition according to claim 6 wherein the chlorofluorocarbon or chlorofluorohydrocarbon is of 1 or 2 carbon atoms and the concentration of insect repelling compound therein is in the range of 1 to 5%.

8. An insect repellent composition according to claim 6 wherein the liquid medium is a hydrocarbon and the composition is under superatmospheric pressure.

9. An insect repellent composition according to claim 1 which is effective to repel insects from sites to which it is applied at a rate of 0.1 to 10 g./sq. m., which comprises 0.2 to 50% of the insect repelling compound in a particulate carrier.

10. An insect repellent composition according to claim 9 wherein the particular carrier is silica and the percentage of insect repelling compound in the composition is in the range of 0.2 to 25% thereof.

11. An insect repellent composition according to claim 9 wherein the particulate carrier is of particulate sizes in the range of 0.12 to 2.4 mm in diameter.

12. An insect repellent composition according to claim 9 wherein the particulate carrier is clay, the insect repelling compound is present in the composition at a concentration in the range of 0.5 to 10% and it was sprayed onto the clay.

13. An insect repellent composition according to claim 9 wherein the particulate carrier is boric acid, the insect repelling compound is present in the composition at a concentration in the range of 0.5 to 10% and it was sprayed onto the boric acid.

* * * * *